United States Patent [19]

Waters

[11] Patent Number: 4,994,070
[45] Date of Patent: Feb. 19, 1991

[54] APPARATUS FOR DILATING A BODY CAVITY

[76] Inventor: Gerard A. Waters, Castletown House, Celbridge, County Kildare, Israel

[21] Appl. No.: 336,040

[22] Filed: Apr. 11, 1989

[51] Int. Cl.$^5$ .............................................. A61M 29/00
[52] U.S. Cl. .................................... 606/191; 606/192; 606/193
[58] Field of Search ........................ 606/191, 192, 193

[56] References Cited

U.S. PATENT DOCUMENTS

| | | | |
|---|---|---|---|
| 3,077,194 | 2/1963 | Walden et al. | 606/191 X |
| 3,192,928 | 7/1965 | Horton | 606/191 |
| 3,841,318 | 10/1974 | Olson | 128/20 |
| 4,237,893 | 12/1980 | Michaels | 606/193 |
| 4,562,832 | 1/1986 | Wilder et al. | 128/20 |
| 4,740,207 | 4/1988 | Kreamer | 606/108 X |

FOREIGN PATENT DOCUMENTS 2154765  11/1971  Fed. Rep. of Germany .
2444450   7/1980  France .

OTHER PUBLICATIONS

European published application 0043218 (Appl. 81302797.6, filed Jun. 22, 1981).

Primary Examiner—Robert A. Hafer
Assistant Examiner—Kerry Owens
Attorney, Agent, or Firm—Tilton, Fallon, Lungmus

[57] ABSTRACT

A vaginal speculum has a sheet member of inherently resilient material capable of being rolled into a normal position in which the member forms a narrow generally elongate shape. The sheet member is expandable under its inherent resilience to a dilated position in which the member forms a hollow generally open ended elongate shape having a substantially continuous sidewall. The sheet member is provided with first and second handle members which are atttached to the sheet member along left and right edges, respectively.

7 Claims, 4 Drawing Sheets

APPARATUS FOR DILATING A BODY CAVITY

The present invention relates to an apparatus for dilating a body cavity. In particular, the invention relates to a vaginal speculum.

Vaginal specula are widely used in gynaecological medicine for many purposes including the opening of the vaginal cavity for inspection of the uterine cervix as in papaniculoru smears. In general, the known types of specula comprise a pair of elongate curved blade members which are pivotted together and movable apart when inserted in the vaginal cavity to dilate the vagina to the desired amount. These instruments are well known to doctors by their inventors names such as Cuscos, Wintertons, Graves, Semm, Ferguson Simm and Auvards. When the blade members have been moved apart in the vagina, there is usually a space defined between the adjacent edges of the blade members. The space which is present between the blade members results in two major problems.

First, the vaginal wall, particularly in obese women, tends to collapse and project through the spaces between the blade members thus obscuring the view of the cervix and the vaginal cavity. In addition, prior to removing the speculum from the vaginal cavity, the blade members are moved together and this often results in pinching of the vaginal wall between the blade members. Other problems and disadvantages of the known types of specula include; due to the complexity of the hinges and locking mechanism they tend to be difficult to produce are expensive, and are difficult to clean and sterilize properly; they tend to be disconcerting to the patient due to the inherent shape of them; following insertion they tend to be uncomfortable to the patient when excessive dilatation is applied; the operation of the instrument is noisy which tends to be distressing to the patient, due to the locking mechanism.

Accordingly, it is an object of the present invention to provide an apparatus for dilating a body cavity and in particular to provide a vaginal speculum which overcomes the abovementioned problems.

According to the present invention there is provided an apparatus for dilating a body cavity comprising, an expandable member having a normal position and a dilated position, in the normal position the member defines a narrow generally elongate shape for insertion in a body cavity, and means to expand the member to its dilated position in which the member forms a hollow generally open ended elongate shape having a substantially continuous sidewall to dilate the body cavity.

An embodiment of the invention will now be described, by way of example, with reference to the accompanying drawings, in which.

Figure 1:
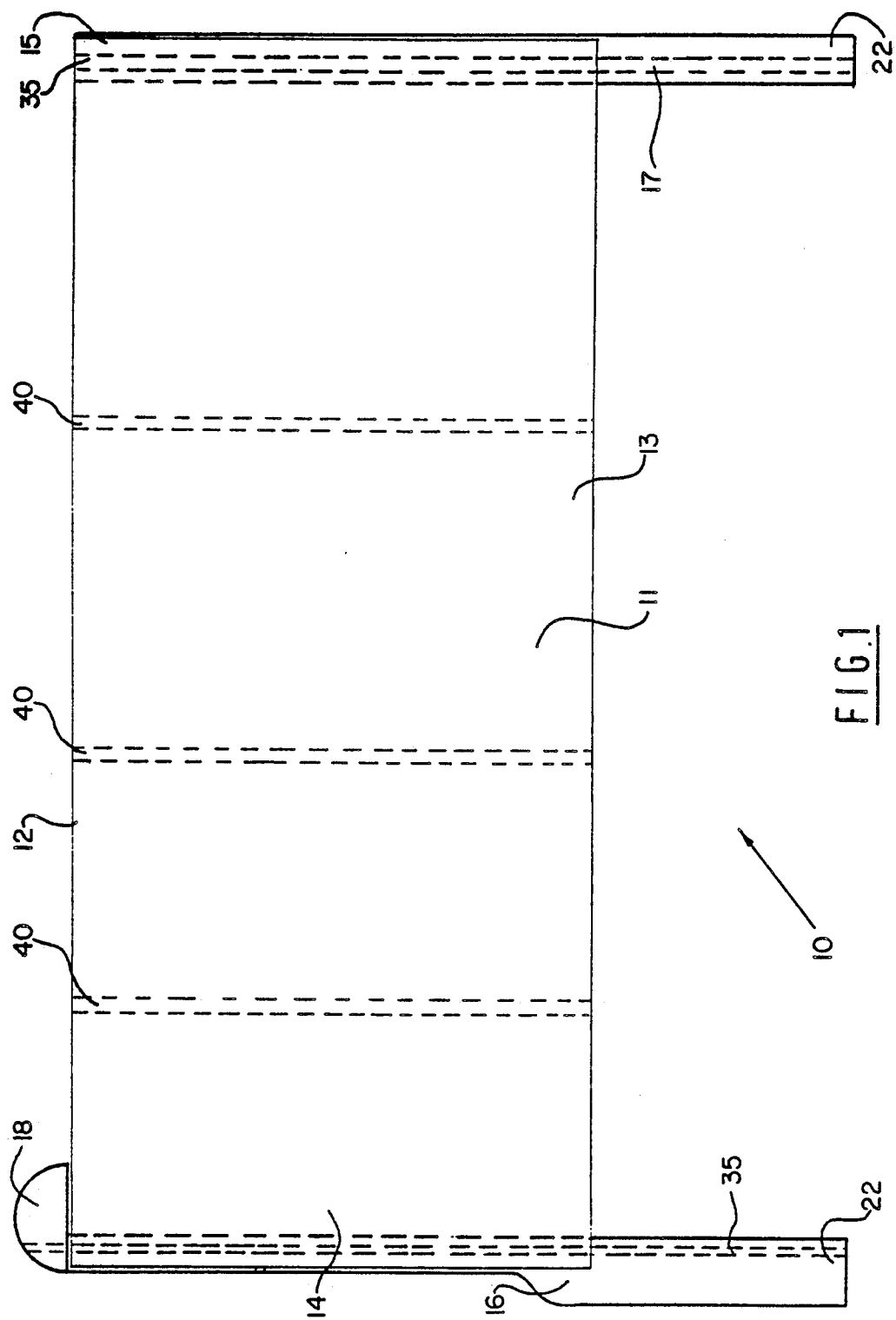
FIG. 1 is a plan view of an apparatus for dilating a body cavity according to the invention, with the apparatus in a fully extended position.

Referring now to the drawings, wherein similar numerals have been used to indicate like parts, there is shown therein an apparatus for dilating a body cavity generally indicated at 10 according to the invention. The apparatus or vaginal speculum 10 comprises a rectangular sheet 11 of plastics or other suitable material having upper and lower edges 12, 13 respectively and left and right side edges 14, 15 respectively. Along each side edge 14, 15 there is fixed by conventional means handles 16, 17 respectively, both of which extend beyond the lower edge 13 of the sheet 11. The handle 16 includes an integrally formed off-centred conical or dome shaped tip 18 which extends slightly towards the other handle 17 as shown in FIG. 1.

Figure 2:
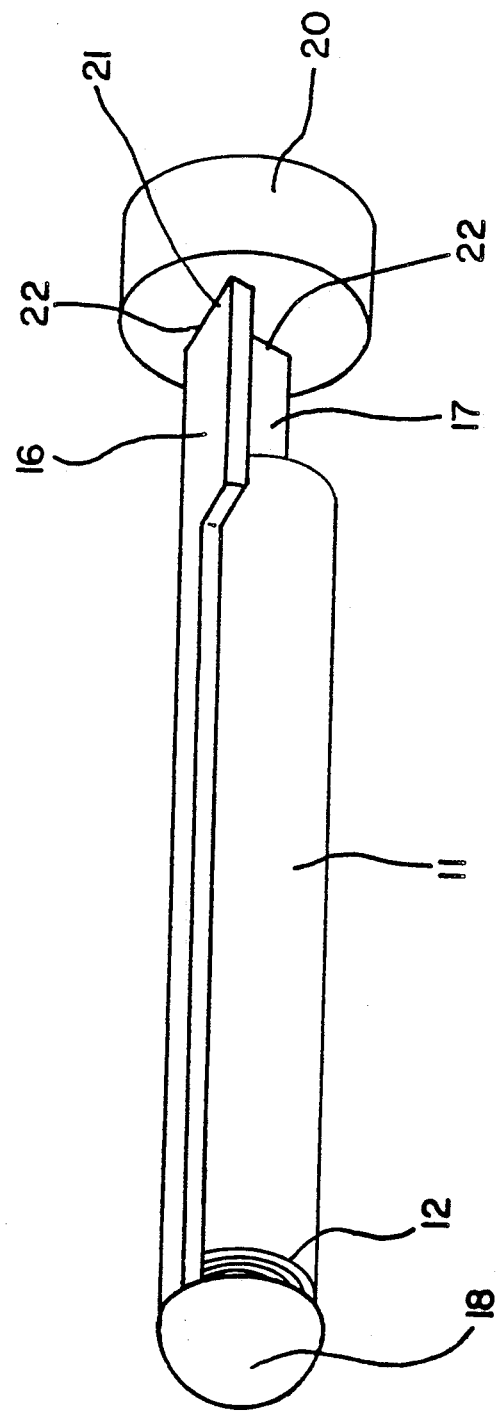
FIG. 2 is a perspective view of the apparatus of FIG. 1 in a normal position.
Figure 3:
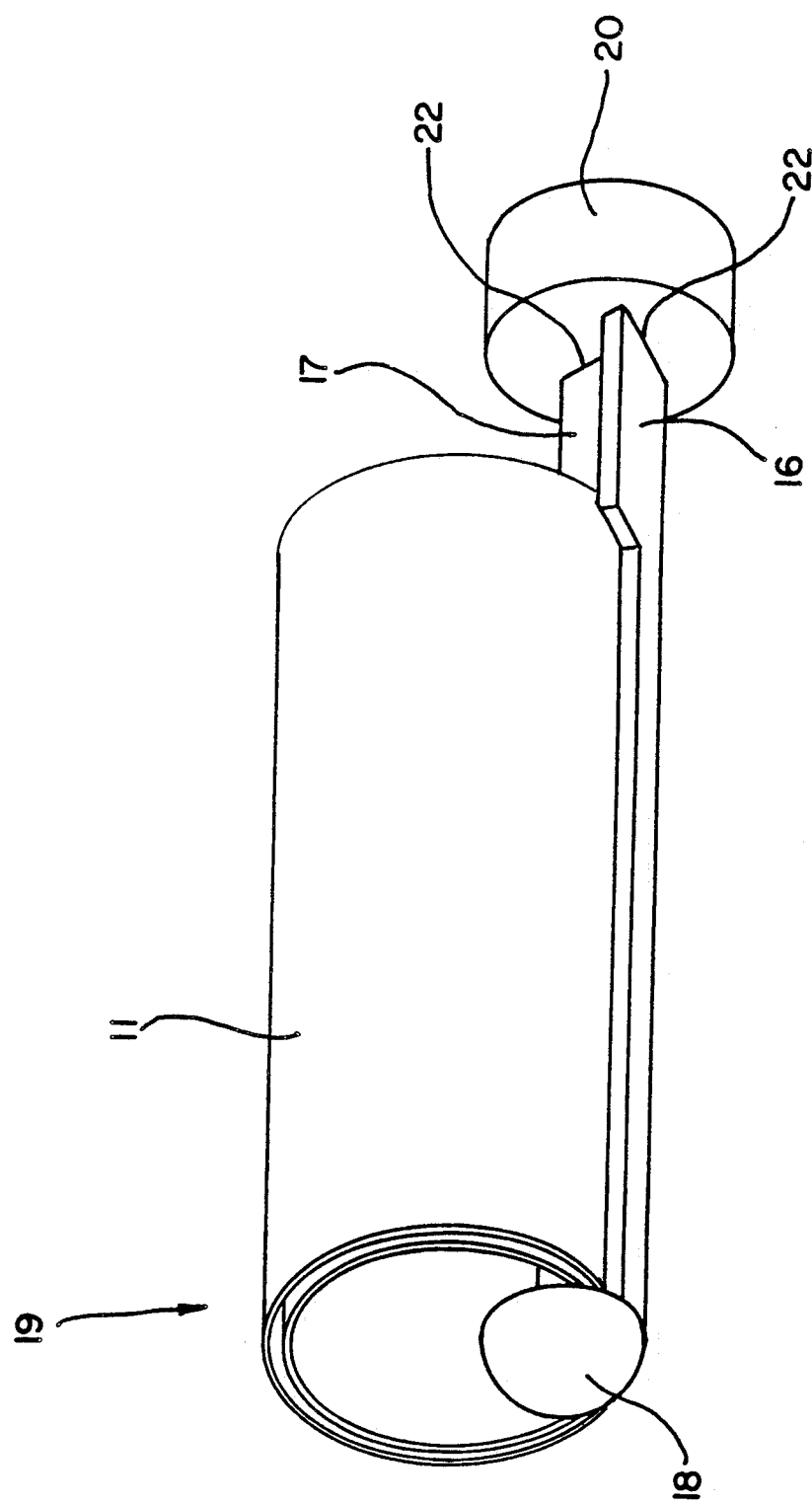
FIG. 3 is a perspective view of the apparatus of FIG. 1 in its dilated position.

The plastics sheet 11 is formed during manufacture to have an inherent resilience causing it to be naturally urged into a partially unrolled dilated cylindrical shape 19 as shown in FIG. 3 having a substantially continuous sidewall. The inherent resilience of the sheet 11 is sufficiently strong enough to enable the apparatus to expand and dilate the vagina of a patient. However, the sheet 11 may be further rolled into a narrow cylindrical shape as illustrated in FIG. 2 for insertion in the vagina in which both the upper edge 12 of the sheet and the upper end of the handle 17 are located behind the conical tip 18 of the handle 16 in what is referred to as the normal position. A collar 20 having a T-shaped recess 21 is provided to secure the apparatus in both the normal and dilated positions by engaging the lower ends 22 of the handles 16, 17 in the T-shaped recess as shown.

With the apparatus in the position of FIG. 2, then by holding the handles 16, 17 with the collar 20 in place, the apparatus is introduced, conical tip 18 first, into the vaginal cavity. Thus, it will be appreciated that the conical tip 18 will allow easy entry of the apparatus with the minimum of discomfort to the patient. The collar 20 is then removed and due to the natural inherent resilience of the sheet 11, the sheet 11 uncoils and expands until it has assumed the position of FIG. 3, thus gradually dilating the vaginal cavity. Only about two thirds of the length of the speculum would normally be inserted into the vagina. The doctor carrying out the inspection can readily manipulate the handles 16, 17 to allow the sheet 11 to uncoil and expand and thus dilate the vaginal cavity slowly. Once the apparatus has assumed the position of FIG. 3, the collar 20 can be engaged on the handles 16, 17 once again to maintain this position of the speculum.

Figure 4:
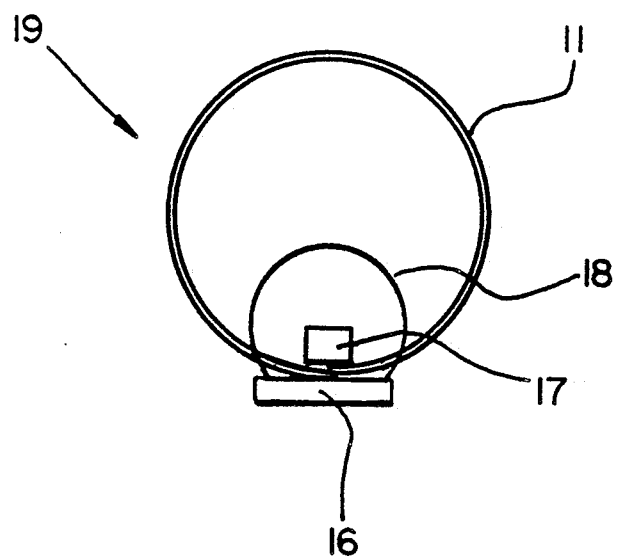
FIG. 4 is an end view of the apparatus of FIG. 3.
Figure 5:
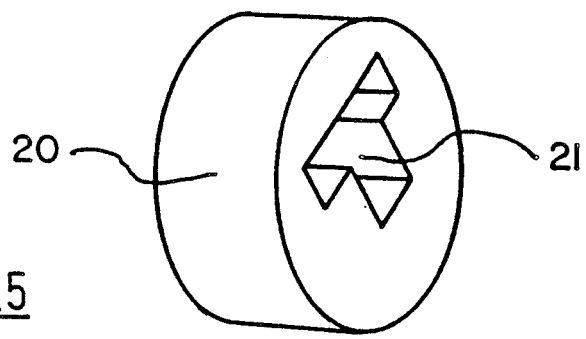
FIG. 5 is a perspective view of one form of securing means according to the invention.

Thus, once in place, the doctor will normally have a clear view of the vaginal cavity and cervix as indicated by the end view of the apparatus in FIG. 4. To remove the apparatus, the procedure may be reversed thus coiling the sheet 11 to the position of FIG. 2.

The handles may be used to conduct light into the vaginal cavity, for example if they are hollow, or include one or more light channels or optical fibres as indicated in dotted outline at 35.

Figure 6:
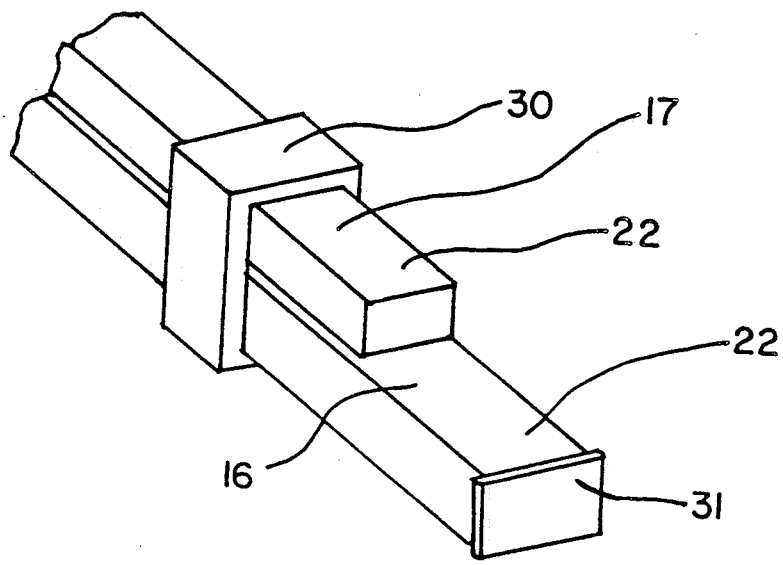
FIG. 6 is a perspective view of another embodiment of securing means according to the invention.

In another embodiment of the invention shown in FIG. 6, the collar 20 has been substituted with a hollow rectangular collar 30 which slips readily over the ends 22 of the handles 16, 17. The handle 16 has a flange 31 formed at its end to prevent the collar 30 from being removed. In addition, it will be noted that the handle 17 is shorter than the handle 16 and this facilitates manipulation of the handles, particularly rotation of one of the handles. The collar 30 can be moved to a position adjacent the flange 31 to rotate the handle 16, and when rotated sufficiently, the collar 30 can be moved forwards again to engage both handles.

In another embodiment of the invention, the conical tip 18 may also have a suitable recess formed therein to receive the upper end of the handle 17, the upper end of the handle 17 extending slightly beyond the edge 12 of the sheet 11. It will be appreciated that the sheet 11 may have fixed thereon or imbedded therein a plurality of light channels, for example optical fibres 40 extending between the upper and lower edges 12, 13 of the sheet to convey light into the vaginal cavity.

A major advantage of the invention is that when in the dilated position of FIG. 3, the apparatus provides a generally continuous cylindrical wall, and no pinching or obscuring of the vaginal cavity can occur. In addition, the apparatus is simple and inexpensive to manufacture and may therefore be disposable. Other advantages of the invention include; in unrolled form it is easy to clean and sterilize; it is simple and small hence less frightening to the patient; it will only dilate to the comfortable circumference of the vagina; it is silent in use and hence less disturbing to the patient; as the vaginal walls are supported there is no obstruction to view of the cervix; it is easily removed due to smooth material surfaces; there is no pinching of the vaginal wall on removal; due to the locking mechanism on the handles, less experience is necessary for use.

It will be appreciated that the invention will have application in both human and veterinary medicine.

I claim:

1. A vaginal speculum comprising a sheet member of inherently resilient material capable of being rolled into a normal position in which the sheet member forms a narrow generally elongate shape, the sheet member being expandable under its inherent resilience to a dilated position in which the sheet member forms a hollow generally open-ended elongate shape having a substantially continuous sidewall, said sheet member being generally rectangular and having upper and lower edges and left and right side edges, a first elongate handle member attached along the left side edge of the sheet member and a second elongate handle member attached along the right side edge of the sheet member, said first and second elongate handle members having lower ends which extend below the lower edge of the sheet member.

2. An apparatus as claimed in claim 1, wherein one of said handle members has an upper end adjacent to the upper edge of the sheet member, said upper end having a dome-shaped tip.

3. An apparatus as claimed in claim 1, wherein there is provided means for securing the handle members together in the normal and dilated positions of the sheet of material.

4. An apparatus as claimed in claim 3, wherein the means for securing the handle members together comprises a collar having a suitable recess to receive the ends of the handle members.

5. An apparatus as claimed in claim 3, wherein said first handle member is longer than said second handle member, and the means for securing the handle members together comprises a hollow collar which engages over the lower ends of the handles.

6. An apparatus as claimed in claim 1, wherein the sheet member includes at least one light guide for conveying light into the body cavity.

7. An apparatus as claimed in claim 1, wherein at least one of said handle members includes a light guide for conveying light into the body cavity.

* * * * *

UNITED STATES PATENT AND TRADEMARK OFFICE
CERTIFICATE OF CORRECTION

PATENT NO. : 4,994,070
DATED : February 19, 1991
INVENTOR(S) : Gerard A. Waters

It is certified that error appears in the above-identified patent and that said Letters Patent is hereby corrected as shown below:

ON TITLE PAGE: [76], in the inventor's address, delete Israel and insert "Ireland"

Signed and Sealed this

Seventh Day of July, 1992

Attest:

DOUGLAS B. COMER

*Attesting Officer*     Acting Commissioner of Patents and Trademarks